United States Patent

Uchida et al.

(10) Patent No.: US 6,376,694 B1
(45) Date of Patent: Apr. 23, 2002

(54) SILOLE DERIVATIVES AND ORGANIC ELECTROLUMINESCENT ELEMENT CONTAINING THE SAME

(75) Inventors: Manabu Uchida; Toshihiro Koike; Takenori Izumizawa, all of Yokohama; Kenji Furukawa, Yokosuka, all of (JP)

(73) Assignee: Chisso Corporation, Osaka (JP)

( * ) Notice: Subject to any disclaimer, the term of this patent is extended or adjusted under 35 U.S.C. 154(b) by 0 days.

(21) Appl. No.: 09/743,426

(22) PCT Filed: Jul. 7, 1999

(86) PCT No.: PCT/JP99/03671

§ 371 Date: Jan. 9, 2001

§ 102(e) Date: Jan. 9, 2001

(87) PCT Pub. No.: WO00/02886

PCT Pub. Date: Jan. 20, 2000

(30) Foreign Application Priority Data

Jul. 9, 1998 (JP) .......................................... 10-210388

(51) Int. Cl.$^7$ ................................................. C07F 7/08
(52) U.S. Cl. ...................... 556/406; 313/504; 313/506; 428/690
(58) Field of Search .................. 556/406; 313/504; 315/501; 428/690

(56) References Cited

U.S. PATENT DOCUMENTS

| 5,498,736 A | * | 3/1996 | Tamao et al. ................ 556/406 |
| 6,169,193 B1 | * | 1/2001 | West et al. .................. 556/406 |

FOREIGN PATENT DOCUMENTS

| DE | 2534713 | 2/1977 |
| DE | 44 42 050 | 5/1996 |
| EP | 793699 | 6/1996 |
| EP | 754691 | 1/1997 |
| JP | 57-144558 | 9/1982 |
| JP | 61-062038 | 3/1986 |
| JP | 61-112164 | 5/1986 |
| JP | 61-124949 | 6/1986 |
| JP | 61-134354 | 6/1986 |
| JP | 61-134355 | 5/1987 |
| JP | 04-212286 | 8/1992 |
| JP | 04-308688 | 10/1992 |
| JP | 04-363891 | 12/1992 |
| JP | 06-001972 | 1/1994 |
| JP | 06-100669 | 4/1994 |
| JP | 06-166746 | 6/1994 |
| JP | 06-267658 | 9/1994 |
| JP | 06-312979 | 11/1994 |
| JP | 07-090256 | 4/1995 |
| JP | 07-097355 | 4/1995 |
| JP | 07-126226 | 5/1995 |
| JP | 07-126615 | 5/1995 |
| JP | 07-179477 | 7/1995 |
| JP | 07-278537 | 10/1995 |
| JP | 07-300489 | 11/1995 |
| JP | 07-331238 | 12/1995 |
| JP | 08-048656 | 2/1996 |
| JP | 08-100172 | 4/1996 |
| JP | 6-87616 | 3/1997 |
| JP | 09-087616 | 3/1997 |
| JP | 9-194487 | 7/1997 |
| JP | 09-194487 | 7/1997 |
| JP | 63-264692 | 11/1998 |
| WO | 96/17035 | 6/1996 |

* cited by examiner

*Primary Examiner*—Paul F. Shaver
(74) *Attorney, Agent, or Firm*—Wenderoth, Lind & Ponack, L.L.P.

(57) ABSTRACT

A specific silole derivative represented by Formula (1) is incorporated into an organic electroluminescent element. Thus, the element can have a high efficiency and a long life.

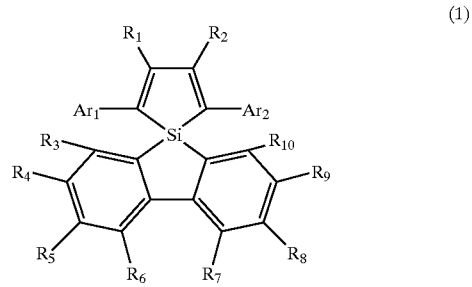

(1)

In Formula (1), $R_1$ and $R_2$ each independently represent a substituted or unsubstituted alkyl, silyl, aryl, heterocyclic or alkenyl group and may be bonded with each other at the respective terminals; $Ar_1$ and $Ar_2$ each independently represent a substituted or unsubstituted aryl or heterocyclic group; and $R_3$ to $R_{10}$ each independently represent a substituted or unsubstituted alkyl, aryl or heterocyclic group and may be bonded with each other at the respective terminals.

8 Claims, No Drawings ic SILOLE DERIVATIVES AND ORGANIC
ELECTROLUMINESCENT ELEMENT
CONTAINING THE SAME

This application is 371 application PCT/JP99/03671 filed Jul. 7, 1999.

TECHNICAL FIELD

The present invention relates to a silole derivative which can be widely applied to electronically functional materials and optically functional materials, and an organic electroluminescent element containing the same.

BACKGROUND ART

Various institutions have tried to apply π electron base organic compounds to optically functional materials and electronically functional materials in various ways.

Among those compounds, a group of π electron base organic compounds having a hetero five-membered ring structure as a fundamental structure, for example, thiophene and pyrrole are known as one of typical π electron base organic compound groups. However, most of their hetero five-membered rings have an electron-donating property, which has limited an application of the compounds to the materials. Accordingly, π electron-accepting compounds have so far been required.

Recently, it has been reported that a silole ring shows an electron-accepting property, and an application thereof to various functional materials is expected. An application of the ring to conductive polymers has been reported in JP-A 6-100669 and JP-A 6-166746, for example.

An application of silole derivatives to organic EL elements making the best use of their electron-accepting property has been reported, for example, in JP-A 9-87616; JP-A 9-194487; Japan Chemical Society, 70 Annual Spring Meeting, Lecture Abstract II, pp. 700, 2D102; Japan Chemical Society, 70 Annual Spring Meeting, Lecture Abstract II, pp. 701, 2D103; Japan Chemical Society, 71 Annual Autumn Meeting, Lecture Abstract, pp. 32, 2P1α21; and Japan Chemical Society, 71 Annual Autumn Meeting, Lecture Abstract, pp. 32, 2P1α22. Among them, several compounds have a suitable electron-accepting property and electron-donating property and also an electroluminescent property, and are therefore applied to electroluminescent materials. However, the compounds described therein do not have a sufficiently high electroluminescent brightness for practical use.

An organic EL element comprises a structure in which an organic compound is interposed between electrodes, and the organic compound used includes a charge-transporting material and an electroluminescent material. In order to prepare an organic EL element having a low power consumption and a high efficacy, it is necessary to use an electroluminescent material having a high electroluminescent efficiency. However, there have been few reports on an electroluminescent characteristic of a silole derivative.

JP-A 7-179477 and JP-A 7-300489, for example, disclose syntheses of various silole derivatives by introducing reactive substituents into the 2- and 5-positions of a silole ring. However, their electroluminescent property is not described therein.

German Patent (DE4442050) discloses a spirosilole derivative applied to an organic EL element, but an electroluminescent characteristic of those compounds is not described at all. The structure thereof is restricted to a dibenzo derivative, and there is no description about a synthetic method or physical property values of a compound having an asymmetric skeleton.

Further, dithienosilole derivatives are described in Chemistry Letters, 1998, 1233, but they have been very poor in performance and low in practicability as an electroluminescent material for an organic EL element.

The present invention has been achieved in light of the problems involved in the conventional techniques described above. An object of the invention is to provide a novel silole derivative having a high electroluminescent efficiency and an organic EL element containing the said silole derivative.

DISCLOSURE OF THE INVENTION

The present inventors have intensively investigated a silole derivative which can solve the preceding problems involved in conventional organic EL elements, and which is applied to various functional materials. As a result, the inventors have found a specific silole derivative and further found that use of the silole derivative provides an organic EL element having a high electroluminescent efficiency, and thus completed the present invention.

More specifically, the present invention comprises structures shown in the following items (1), (2), (3), (4) and (5):

(1) A silole derivative represented by the following Formula (1):

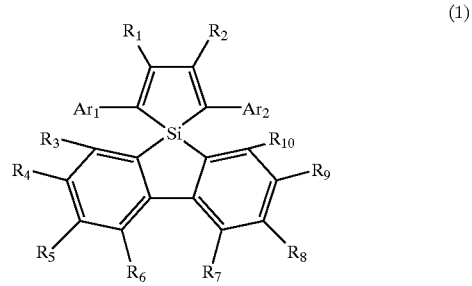

wherein $R_1$ and $R_2$ each independently represent a substituted or unsubstituted alkyl, silyl, aryl, heterocyclic or alkenyl group and may be bonded with each other at the respective terminals; $Ar_1$ and $Ar_2$ each independently represent a substituted or unsubstituted aryl or heterocyclic group; and $R_3$ to $R_{10}$ each independently represent a substituted or unsubstituted alkyl, aryl or heterocyclic group and may be bonded with each other at the respective terminals.

(2) A silole derivative represented by the following Formula (2):

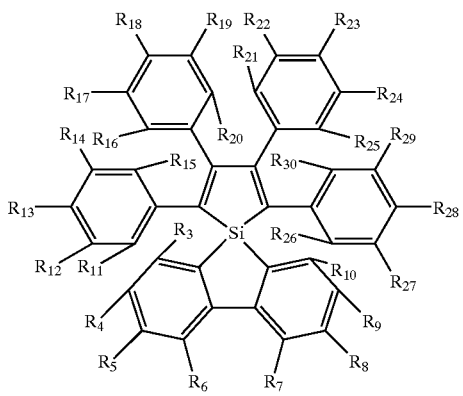

(2)

wherein $R_{11}$ to $R_{30}$ each independently represent a substituted or unsubstituted alkyl, aryl or heterocyclic group and may be bonded with each other at the respective terminals; and $R_3$ to $R_{10}$ each independently represent a substituted or unsubstiituted alkyl, aryl or heterocyclic group and may be bonded with each other at the respective terminals.

(3) A silole derivative represented by the following Formula (3):

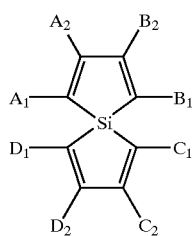

(3)

wherein $A_1$ and $A_2$ are bonded with each other to form a 5- or 6-membered ring; $B_1$ and $B_2$ are bonded with each other to form a 5- or 6-membered ring; $C_1$ and $C_2$ are bonded with each other to form a 5- or 6-membered ring; and $D_1$ and $D_2$ are bonded with each other to form a 5- or 6-membered ring.

(4) A silole derivative represented by the following Formula (4):

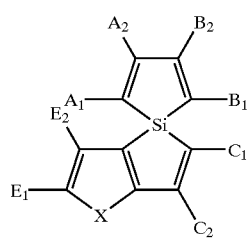

(4)

wherein $A_1$ and $A_2$ are bonded with each other to form a 5- or 6-membered ring; $B_1$ and $B_2$ are bonded with each other to form a 5- or 6-membered ring; $C_1$ and $C_2$ are bonded with each other to form a 5- or 6-membered ring; $E_1$ and $E_2$ are bonded with each other to form a 5- or 6-membered ring; X represents oxygen, sulfur or NR; and R represents hydrogen, an alkyl group or an aryl group.

(5) An organic electroluminescent element containing the silole derivative as described in at least one of the items (1), (2), (3) and (4) for an electroluminescent layer.

BEST MODE FOR CARRYING OUT THE INVENTION

The present invention shall be explained below in details.

Specific examples of the silole derivative of the present invention represented by Formula (1) include compounds represented by the following Formulas (5) to (15):

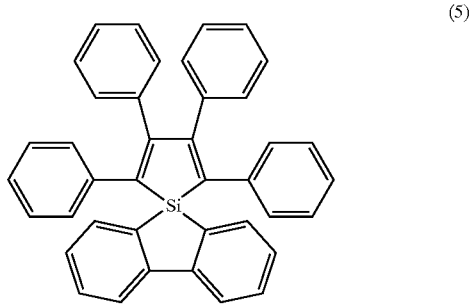

(5)

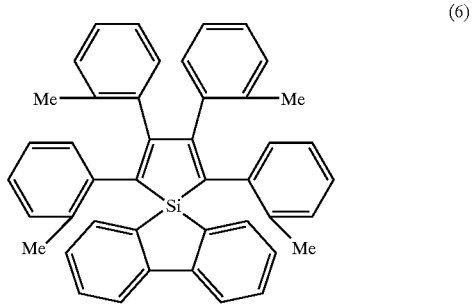

(6)

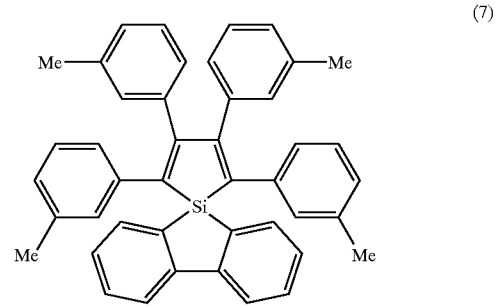

(7)

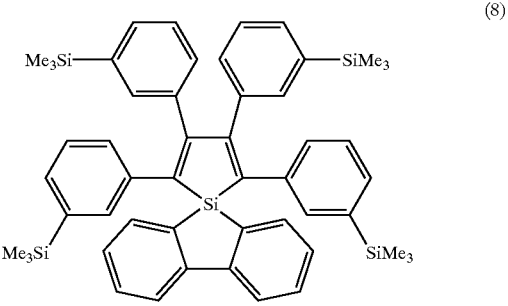

(8)

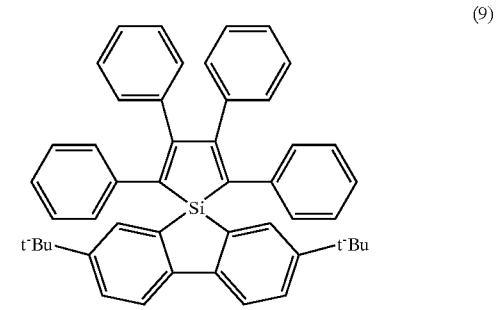

(9)

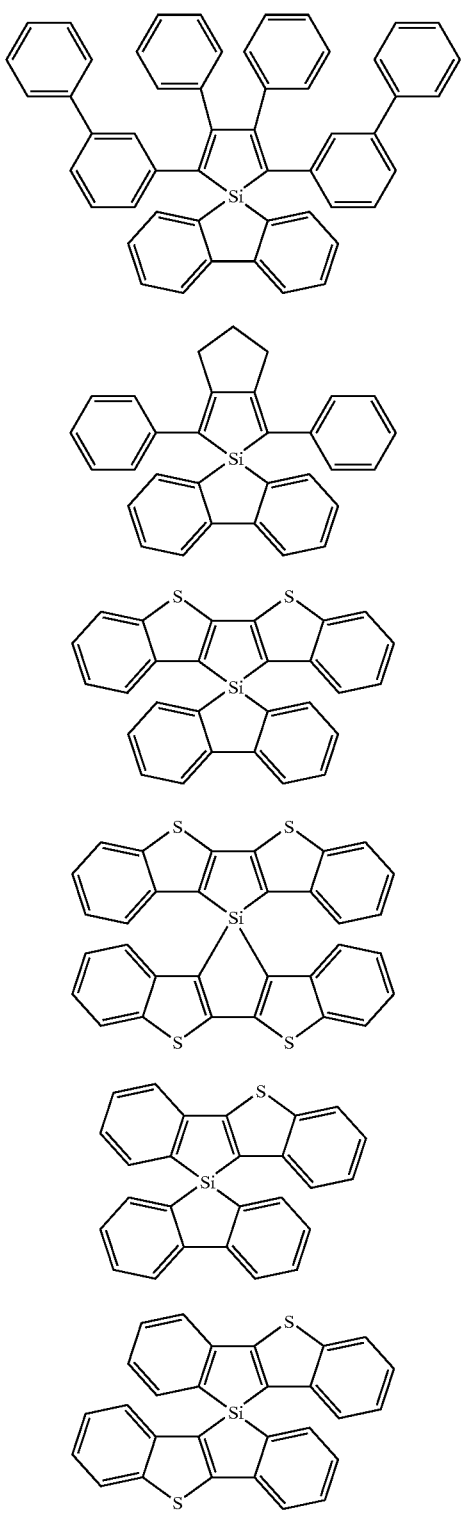

The silole derivative of the present invention can be obtained, for example, by the production process, which comprises reacting a diene derivative represented by Formula (16)

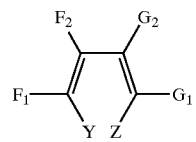

wherein $F_2$ and $G_2$ each independently represent a substituted or unsubstituted alkyl, silyl, aryl, heterocyclic or alkenyl group and may be bonded with each other at the respective terminals; $F_1$ and $G_1$ each independently represent a substituted or unsubstituted aryl or heterocyclic group; $F_1$ and $F_2$ may be bonded with each other to form a 5- or 6-membered ring; $G_1$ and $G_2$ may be bonded with each other to form a 5- or 6-membered ring; and Y and Z each independently represent a halogen atom; with a base and subsequently reacting it with a silane derivative.

In the above production process, the base to be used includes, for example, organic lithium reagents such as n-butyllithium, tert-butyllithium and phenyllithium, and Grignard reagents such as magnesium and magnesium bromide. The solvent to be used shall not specifically be restricted as long as it is inactive to these bases, and usually used are ethers such as diethyl ether and tetrahydrofuran (hereinafter referred to as THF) and aromatics such as benzene and toluene.

The silole derivative of the present invention, particularly that represented by Formula (2) is also obtained by reacting an acetylene derivative represented by Formula (17)

wherein $Ar_1$ and $Ar_2$ each independently represent a substituted or unsubstituted aryl or heterocyclic group, with metallic lithium and subsequently reacting it with a silane derivative. The solvent to be used shall not specifically be restricted as long as it is inactive to these bases, and ether solvents such as diethyl ether and THF are usually used.

In the production processes for the silole derivatives represented by Formulas (2), (3) and (4), the silane derivatives to be used include halogenated silafluorenes such as 9,9-dichlorosilafluorene and 2,7-di-tert-butyl-9,9-dichlorosilafluorene and alkoxysilanes such as 9,9-dimethoxysilafluorene.

The reaction is carried out preferably in inert gas, and nitrogen and argon, etc. are used. The reaction temperature shall not specifically be restricted, but an extent of −78 to 120° C. is usually preferred. In this reaction, the reaction time shall not specifically be restricted, and the reaction may be stopped when the reaction proceeds sufficiently. The reaction can be traced by an ordinary analytical means such as NMR and chromatography to determine the optimum end point of the reaction.

Further, the silole derivatives of the present invention represented by Formulas (1) and (2) can be synthesized as well by converting the resulting compound by a usually known synthetic method.

The substituent may be introduced either before or after forming the silole ring.

The substituent introduced into the silole derivative of the present invention thus obtained includes an alkyl group such as methyl, ethyl, n-propyl, isopropyl, cyclopentyl and tert-butyl; an alkenyl group such as vinyl, allyl, butenyl and styryl; a silyl group such as trimethylsilyl, dimethyl-tert-butylsilyl, trimethoxysilyl and triphenylsilyl; an aryl group such as phenyl, naphthyl, anthracenyl, biphenylyl, toluyl, pyrenyl, perylenyl, anisyl, terphenyl and phenanthrenyl; and a heterocycle such as hydrofuryl, hydropyrenyl, dioxanyl, thienyl, furyl, oxazolyl, oxadiazolyl, thiazolyl, thiadiazolyl, acridinyl, quinolyl, quinoxaloyl, phenanthrolyl, benzothienyl, benzothiazolyl, indolyl, silacyclopentadienyl and pyridyl.

These substituents may be bonded with each other in optional positions to form rings.

The silole derivative of the present invention can be widely applied not only to electroluminescent materials but also to electronically functional materials and optically functional materials by making use of the electronic properties originating in the silole ring.

The organic EL element of the present invention can have a structure in various forms and basically has a structure in which an organic layer containing the silole derivatives represented by Formulas (1) and (2) is interposed between a pair of electrodes (anode and cathode). If necessary, a hole-injecting material, a hole-transporting material, an electroluminescent material, an electron-injecting material, an electron-transporting material, etc. can be added to the silole derivative layer described above. Further, other electroluminescent materials can be added to this electroluminescent layer so as to emit light having a different wavelength and to elevate the electroluminescent efficiency.

These hole-injecting material, hole-transporting material, electro-luminescent material, electron-injecting material and electron-transporting material can be laminated on a layer containing the silole derivative to form a hole-injecting layer, a hole-transporting layer, an electroluminescent layer, an electron-injecting layer and an electron-transporting layer, respectively.

The specific structure includes (1) anode/silole derivative layer of the present invention/cathode, (2) anode/hole-injecting layer/silole derivative layer of the present invention/cathode, (3) anode/silole derivative layer of the present invention/electron-injecting layer/cathode, (4) anode/hole-injecting layer/silole derivative layer of the present invention/electron-injecting layer/cathode, (5) anode/hole-injecting layer/silole derivative layer of the present invention/electron-transporting layer/interface layer/cathode, (6) anode/hole-injecting layer/hole-transporting layer/silole derivative layer of the present invention/electron-injecting layer/cathode and (7) anode/hole-injecting layer/hole-transporting layer/silole derivative layer of the present invention/electron-injecting layer/interface layer/cathode.

In these cases, a hole-injecting layer, an electron-injecting layer, a hole-transporting layer, an electron-transporting layer and an interface layer are not necessarily required, but these layers can raise the electroluminescent efficiency.

The organic EL element of the present invention is preferably supported on a substrate whatever structure described above it may have. Any substrate may be used as long as it has a good mechanical strength, heat stability and transparency. Glass, a transparent film, etc. can be used therefor.

Metal, alloy, electroconductive compounds and a mixture thereof each having a larger work function than 4 eV can be used as an anodic material for the organic EL element of the present invention. Specific examples thereof include metal such as Au and conductive transparent materials such as CuI, indium tin oxide (hereinafter referred to as ITO), $SnO_2$ and ZnO.

Metal, alloy, electroconductive compound sand a mixture thereof each having a smaller work function than 4 eV can be used as the cathodic material. Specific examples thereof include calcium, magnesium, lithium, aluminum, magnesium alloy, lithium alloy and aluminum alloy, and the mixture thereof includes aluminum/lithium, magnesium/silver and magnesium/indium.

In order to obtain efficient electroluminescence of the organic EL element, at least one of the electrodes preferably has a light transmittance of 10% or more. A sheet resistance of the electrode is controlled preferably to several hundred Ω/mm or less. The film thickness is selected in a range of usually 10 nm to 1 μm, preferably 10 to 400 nm, depending on a property of the electrode material. Such electrodes can be prepared by forming a thin film by a method such as deposition and sputtering using the electrode substances described above.

Preferred interface layers are those promoting injection of an electron from cathode. Also preferred are those preventing an electron hole from flowing into the cathode. They are selected according to compatibility with a material used for the cathode. Specific examples thereof include lithium fluoride, magnesium fluoride and calcium fluoride.

In the organic EL element of the present invention, materials used for the hole-injecting material, the hole-transporting material, the electro-luminescent material, the electron-injecting material and the electron-transporting material preferably have a Tg of 80° C. or higher, more preferably 100° C. or higher.

The other hole-injecting material and hole-transporting material used for the organic EL element of the present invention may optionally be selected from compounds which have been conventionally used as an electron-transporting material for an electron hole in a photoconductive material, and publicly known compounds which are used for a hole-injecting layer and a hole-transporting layer of, an organic EL element.

Those include, for example, carbazole derivatives (N-phenylcarbazole, polyvinylcarbazole, etc.), triarylamine derivatives (TPD, polymers having aromatic tertiary amine in a principal chain or a side chain, 1,1-bis(4-di-p-tolylaminophenyl)cyclohexane, N,N'-diphenyl-N,N'-dinaphthyl-4,4'-diaminobiphenyl (hereinafter abbreviated as NPD), 4,4',4"-tris{N-(3-methylphenyl)-N-phenylamino}triphenylamine, compounds described in Journal of the Chemical Society, Chemical Communication, pp. 2175, 1996, compounds described in JP-A 57-144558, JP-A 61-62038, JP-A 61-124949, JP-A 61-134354, JP-A 61-134355, JP-A 61-112164, JP-A 4-308688, JP-A 6-312979, JP-A 6-267658, JP-A 7-1-5 90256, JP-A 7-97355, JP-A 6-1972, JP-A 7-126226, JP-A 7-126615, JP-A 7-331238, JP-A 8-100172 and JP-A 8-48656, and star-burst amine derivatives described in Advanced Material, vol. 6, pp. 677, 1994), stilbene derivatives (those described in Japan Chemical Society, 72 Annual Spring Meeting, Lecture Abstract (II), pp. 1392, 2PB098), phthalocyanine derivatives (non-metallic, copper phthalocyanine, etc.), and polysilanes.

The hole-injecting layer and the hole-transporting layer in the organic EL element of the present invention may be constituted from a single layer or plural layers containing at least one of the compounds described above or may be formed by laminating plural layers containing different kinds of the compounds.

The other electron-injecting material and electron-transporting material used for the organic EL element of the present invention shall not specifically be restricted, and may optionally be selected from compounds which have been conventionally used as an electron-transferring compound in a photoconductive material, and publicly known compounds which are used for an electron-injecting layer and an electron-transporting layer of an organic EL element.

Preferred examples of such an electron-transferring compound include diphenylquinone derivatives (those described in Electrophotographic Institute Report, 30, 3 (1991)), perylene derivatives (those described in J. Apply. Phys., 27, 269 (1988)), oxadiazole derivatives (those described in the literatures described above, Jpn. J. Apply. Phys., 27, L713 (1988) and Appl. Phys. Lett., 55 1489 (1989)), thiophene derivatives (those described in JP-A 4-212286), triazole derivatives (those described in Jpn. J. Appl. Phys., 32, L917 (1993)), thiadiazole derivatives (those described in 43 Annual Meeting of The Society of Polymer, Japan, Lecture Abstract, (III) Pla007), metal complexes of oxine derivatives (those described in Electronic Information and Communication Institute, Technical Research Report, 92 (311), 43 (1992)), polymers of quinoxaline derivatives (those described in Jpn. J. Appl. Phys., 33, L250 (1994)), and phenanthroline derivatives (those described in 43 Forum of The Society of Polymer, Japan, Lecture Abstract, 14J07).

The other electroluminescent material used for the electroluminescent layer of the organic EL element of the present invention are publicly known electroluminescent materials such as daylight fluorescent materials, fluorescent whitening agents, laser pigments, organic scintillators and various fluorescent analytical reagents which are described in "Optically Functional Material" of High Molecular Functional Material Series, p. 236 (1991), Kyoritsu Publication edited by The Society of Polymer, Japan.

Specifically, preferred are polycyclic condensed compounds such as anthracene, phenanthrene, pyrene, chrysene, perylene, coronene, rubrene and quinacridone, oligophenylene compounds such as quarter phenyl, scintillators for liquid scintillation such as 1,4-bis(2-methylstyryl)benzene, 1,4-bis(4-methylstyryl)benzene, 1,4-bis(4-methyl-5-phenyl-2-oxazolyl)benzene, 1,4-bis(5-phenyl-2-oxazolyl)benzene, 2,5-bis(5-tertiary-butyl-2-benzoxazolyl)thiophene, 1,4-diphenyl-1,3-butadiene, 1,6-diphenyl-1,3,5-hexatriene and 1,1,4,4-tetraphenyl-1,3-butadiene, metal complexes of oxine derivatives described in JP-A 63-264692, coumarin dyes, dicyanomethylenepyran dyes, dicyanomethylenethiopyran dyes, polymethine dyes, oxobenzanthracene dyes, xanthene dyes, carbostyryl dyes and perylene dyes, oxazine compounds described in German Patent 2534713, stilbene derivatives described in 40 Applied Physics-Related Associated Meeting, Lecture Abstract, 1146 (1993), spiro compounds described in JP-A 7-278537 and oxadiazole compounds described in JP-A 4-363891.

The respective layers constituting the organic EL element of the present invention can be prepared by forming thin films from the materials by a conventionally known method such as a vapor deposition method, a spin coating method and a casting method.

The film thickness of the respective layers thus formed shall not specifically be restricted and can suitably be selected according to the properties of the materials. It is usually selected in a range of 2 to 5000 nm.

When the vapor deposition method is used to form the material into a thin film, the depositing conditions thereof are different depending on the kind of the silole derivative, the crystalline structure and the associated structure of the intended molecular built-in film. In general, it is desirable that they are suitably selected in the ranges of a boat-heating temperature of 50 to 400° C., a vacuum degree of $10^{-6}$ to $10^{-3}$ Pa, a depositing speed of 0.01 to 50 nm/second, a substrate temperature of −150 to +300° C. and a film thickness of 5 nm to 5 $\mu$m.

A production process for the organic EL element comprising the anode/silole derivative layer/cathode described above shall be explained as one example of a process for producing the organic EL elements containing the silole derivatives of the present invention represented by Formulas (1) and (2). A thin film comprising a material for an anode is formed on a suitable substrate by a deposition method so that a film thickness should be in a range of 1 $\mu$m or less, preferably 10 to 200 nm to thereby form an anode, and then a thin film of the silole derivative is formed on this anode to prepare an electroluminescent layer. A thin film comprising a material for a cathode is formed on this electroluminescent layer by the deposition method so that a film thickness should be 1 $\mu$m or less to form a cathode, whereby the intended organic EL element is obtained.

In the production of the organic EL element described above, the production order can be inverted, so that the cathode, the electroluminescent layer and the anode may be produced in this order.

When applying a DC voltage to the organic EL element thus obtained, it may be applied with the anode set to a positive polarity and the cathode set to a negative polarity. If applying a voltage of approximately 2 to 40 V, elelctroluminescence can be observed from the transparent or translucent electrode side (anode or cathode and both).

This organic EL element emits light as well when applying an AC voltage. Any waveform of the AC may be applied.

EXAMPLES

The present invention shall specifically be explained with reference to the following examples, but the present invention shall not be restricted by the examples.

Example 1

Synthesis of the compound represented by Formula (5)

Under argon flow, 83 mg of lithium was added to a 10 ml ether solution of 2.139 g of diphenylacetylene. After stirring for 7 hours, 16 ml of THF was added, and then a 14 ml THF solution of 1.507 g of 9,9-dichlorosilafluorene was dropwise added thereto. After stirring for 16 hours at room temperature, 20 ml of water was added. 100 ml of toluene was added to extract an organic layer. Further, 50 ml of toluene was added to a separated aqueous layer to extract an organic layer again. Then, both organic layers were put together and dried on magnesium sulfate, and low boiling matters were removed by distillation under reduced pressure. The residue was purified by means of silica gel column chromatography (eluting solvent: heptane/toluene) and then recrystallized from a mixed solvent of 40 ml of heptane and 10 ml of toluene to obtain 1.12 g of the intended substance. The yield was 35%. This compound emitted green fluorescence in a solid state.

$^1$H-NMR (CDCl$_3$) δ=6.67–6.69 (m, 4H), 6.82–6.86 (m, 6H), 6.91–6.94 (m, 4H), 7.05–7.08 (m, 6H), 7.27 (dd, 2H), 7.46 (dt, 2H), 7.77 (bd, 2H), 7.85 (d, 2H).

Example 2

Synthesis of the compound represented by Formula (6)

The compound was synthesized by the same method as in Example 1, except that bis(2-methylphenyl)acetylene was substituted for diphenylacetylene used in Example 1.

$^1$H-NMR (CDCl$_3$) δ=2.0 (s, 6H), 2.04 (s, 6H), 2.10 (s, 6H), 2.30; (s, 6H), 6.7–7.9 (m, 48H).

The compound was obtained in the form of a mixture of the meso compound and the racemic compound.

Example 3
Synthesis of the compound represented by Formula (7)

The compound was synthesized by the same method as in Example 1, except that bis(3-methylphenyl)acetylene was substituted for diphenylacetylene used in Example 1.

Example 4
Synthesis of the compound represented by Formula (8)

The compound was synthesized by the same method as in Example 1, except that bis(3-trimethylsilylphenyl)-acetylene was substituted for diphenylacetylene used in Example 1.

Example 5
Synthesis of the compound represented by Formula (9)

The compound was synthesized by the same method as in Example 1, except that 2,7-di-tertiary-butyl-9,9-dichlorosilafluorene was substituted for 9,9-dichlorosilafluorene used in Example 1.

Example 6
Synthesis of the compound represented by Formula (10)

3.4 ml of a hexane solution of n-butyllithium (1.6 mol/l) was added to a 30 ml THF solution of 3.81 g of 2,3-diphenyl-1,4-diiodo-1,4-di(metabiphenyl) butadiene at −78° C. under argon flow. After stirring for 30 minutes, 14 ml of a THF solution of 9,9-dichlorosilafluorene (1.256 g) was dropwise added thereto. Then, the temperature was allowed to rise to room temperature. After stirring for 16 hours, 50 ml of water was added. 100 ml of toluene was added to extract an organic layer. Further, 50 ml of toluene was added to a separated aqueous layer to extract an organic layer again. Then, both organic layers were put together and dried on magnesium sulfate, and low boiling matters were removed by distillation under reduced pressure. The residue was purified by means of silica gel column chromatography (eluting solvent: heptane/toluene) and then recrystallized from a mixed solvent of heptane and ethyl acetate to obtain 0.989 g of the intended substance. The yield was 28%.

Example 7
Synthesis of the compound represented by Formula (11)

The compound was synthesized by the same method as in Example 6, except that 1,4-diiodo-1,4-diphenylbutadiene was substituted for 2,3-diphenyl-1,4-diiodo-1,4-di (metabiphenyl)butadiene used in Example 6.

Example 8
Synthesis of the compound represented by Formula (12)

The compound was synthesized by the same method as in Example 6, except that 3,3'-dibromo-2,2'-bibenzothiophene was substituted for 2,3-diphenyl-1,4-diiodo-1,4-di (metabiphenyl)butadiene used in Example 6.

$^1$H-NMR (CDCl$_3$) δ=7.1–7.3 (m, 8H), 7.4–7.6 (m, 4H), 7.8–7.9 (m, 2H), 8.02 (d, 2H).

Example 9

ITO was deposited in a thickness of 100 nm on a glass substrate of 25 mm×75 mm×1.1 mm by a deposition method, which was used as a transparent supporting substrate (manufactured by Tokyo Sanyo Vacuum Co., Ltd.). This transparent supporting substrate was fixed on a substrate holder of a commercially available depositing apparatus (manufactured by Sinku Kiko Co., Ltd.), and equipped with a quartz crucible containing N,N'-dinaphthyl-N,N'-diphenylbenzidine (hereinafter abbreviated as NPD), a quartz crucible containing the compound represented by Formula (3) synthesized in Example 1, a quartz crucible containing 1,1-dimethyl-2,5-bis{2-(2-pyridyl) pyridyl}-3,4-diphenylsilacyclopentadiene (hereinafter referred to as PYPY), a graphite crucible containing magnesium and a graphite crucible containing silver.

The pressure was reduced to $1\times10^{-3}$ Pa in the vacuum chamber, and the crucible containing NPD was heated. NPD was deposited so that the film thickness should be 50 nm, whereby a hole-transporting layer was formed. Then, the crucible containing the compound synthesized in Example 1 was heated. The compound was deposited so that the film thickness should be 15 nm, whereby an electroluminescent layer was formed. Subsequently, the crucible containing PYPY was heated. PYPY was deposited so that the film thickness should be 35 nm, whereby an electron-transporting layer was formed. The depositing speed was 0.1 to 0.2 nm/second.

The pressure was then reduced to $2\times10^{-4}$ Pa in the vacuum chamber, and the graphite crucibles were heated. Magnesium and silver were simultaneously deposited at a depositing speed of 1.2 to 2.4 nm/second and 0.1 to 0.2 nm/second, respectively, to form an alloy electrode of 150 nm comprising magnesium and silver on the organic layer, whereby an organic EL element was obtained.

A DC voltage was applied with the ITO electrode set to an anode and the alloy electrode of magnesium and silver set to a cathode. A current of about 1 mA/cm$^2$ flowed and a green light having a brightness of about 100 cd/m$^2$ and a wavelength of 514 nm was emitted.

Example 10

The transparent supporting substrate used in Example 9 was fixed on the substrate holder of the depositing apparatus, and equipped with a quartz crucible containing N,N'-dinaphthyl-N,N'-diphenylbenzidine (hereinafter abbreviated as NPD), a quartz crucible containing the compound represented by Formula (12) synthesized in Example 8, a quartz crucible containing 1,1-dimethyl-2,5-bis{2-(2-pyridyl) pyridyl}-3,4-diphenylsilacyclopentadiene (hereinafter referred to as PYPY), a graphite crucible containing magnesium and a graphite crucible containing silver.

The pressure was reduced to $1\times10^{-3}$ Pa in the vacuum chamber, and the crucible containing NPD was heated. NPD was deposited so that the film thickness should be 50 nm, whereby a hole-transporting layer was formed. Then, the crucible containing the compound synthesized in Example 8 was heated. The compound was deposited so that the film thickness should be 15 nm, whereby an electroluminescent layer was formed. Subsequently, the crucible containing PYPY was heated. PYPY was deposited so that the film thickness should be 35 nm, whereby an electron-transporting layer was formed. The depositing speed was 0.1 to 0.2 nm/second.

The pressure was then reduced to $2\times10^{-4}$ Pa in the vacuum chamber, and the graphite crucibles were heated. Magnesium and silver were simultaneously deposited at a depositing speed of 1.2 to 2.4 nm/second and 0.1 to 0.2 nm/second, respectively, to form an alloy electrode of 150 nm comprising magnesium and silver on the organic layer, whereby an organic EL element was obtained.

A DC voltage was applied with the ITO electrode set to an anode and the alloy electrode of magnesium and silver set to a cathode. A current of about 6 mA/cm$^2$ flowed and a blue light having a brightness of about 100 cd/m$^2$ and a wavelength of 496 nm was emitted.

Comparative Example 1

An element was prepared by the same method as in Example 9, except that 9,9'-silaspirobifluorene was substituted for the compound represented by Formula (5) synthesized in Example 1.

A DC voltage was applied with the ITO electrode set to an anode and the alloy electrode of magnesium and silver set to a cathode. A current of about 1 MA/cm² flowed and a green light having a brightness of about 20 cd/m² and a wavelength of 522 nm was emitted.

The luminescent brightness was reduced to about 1/5 as compared with that obtained in Example 8.

Comparative Example 2

An element was prepared by the same method as in Example 8, except that 9,9'-silaspirobifluorene was substituted for the compound represented by Formula (3) synthesized in Example 1.

A DC voltage was applied with the ITO electrode set to an anode and the alloy electrode of magnesium and silver set to a cathode. A current of about 1 mA/cm² flowed and a purple light having a brightness of about 5 cd/m² and a wavelength of 425 nm was emitted. This emitted light originated in NPD but not in 9,9'-silaspirobifluorene.

The luminescent brightness was reduced to about 1/20 as compared with that obtained in Example 8.

Comparative Example 3

An element was prepared by the same method as in Example 8, except that 1-allyl-1,2,3,4,5-pentaphenyl-silacyclopentadiene was substituted for the compound represented by Formula (3) synthesized in Example 1.

A DC voltage was applied with the ITO electrode set to an anode and the alloy electrode of magnesium and silver set to a cathode. A current of about 1 mA/cm² flowed and a green light having a brightness of about 6 cd/M² and a wavelength of 503 nm was emitted.

The luminescent brightness was reduced to about 1/17 as compared with that obtained in Example 8.

Example 11

The transparent supporting substrate used in Example 9 was fixed on the substrate holder of the depositing apparatus, and equipped with a quartz crucible containing N,N'-dinaphthyl-N,N'-diphenylbenzidine (hereinafter abbreviated as NPD), a quartz crucible containing the compound represented by Formula (12) synthesized in Example 8, a quartz crucible containing 9,9'-spirobisilafluorene, a quartz crucible containing 1,1-dimethyl-2,5-bis{2-(2-pyridyl) pyridyl}-3,4-20 diphenylsilacyclopentadiene (hereinafter referred to as PYPY), a graphite crucible containing magnesium and a graphite crucible containing silver.

The pressure was reduced to $1 \times 10^{-3}$ Pa in the vacuum chamber, and the crucible containing NPD was heated. NPD was deposited so that the film thickness should be 50 nm, whereby a hole-transporting layer was formed. Then, the crucible containing the compound synthesized in Example 8 and the quartz crucible containing 9,9'-spirobisilafluorene were heated at the same time. The compounds were deposited so that the film thickness should be 15 nm, whereby an electroluminescent layer was formed. Subsequently, the crucible; containing PYPY was heated. PYPY was deposited so that the film thickness should be 35 nm, whereby an electron-transporting layer was formed. The contents of the compounds in the electroluminescent layer were controlled by adjusting the depositing speeds during the formation of the electroluminescent layer. The content of the compound represented by Formula (12) synthesized in Example 8 was 2% by weight.

Then, the pressure was reduced to $2 \times 10^{-4}$ Pa in the vacuum chamber, and the graphite crucibles were heated. Magnesium and silver were simultaneously deposited at a depositing speed of 1.2 to 2.4 nm/second and 0.1 to 0.2 nm/second, respectively, to form an alloy electrode of 150 nm comprising magnesium and silver on the organic layer, whereby an organic EL element was obtained.

A DC voltage was applied with the ITO electrode set to an anode and the alloy electrode of magnesium and silver set to a cathode. A current of about 5 mA/cm² flowed and a blue light originating in the compound represented by Formula (12) and having a brightness of about 100 cd/m² and a wavelength of 470 nm was emitted.

Industrial Applicability

The silole derivative of the present invention has a high electroluminescent efficiency and is therefore suited to an electroluminescent material for an organic EL element. It is also useful as a photoelectrically functional material such as electrophotographic and non-linear optical materials and a conductive material. Further, the organic EL element of the present invention contains an electroluminescent material having a high electroluminescent efficiency, and therefore, it can provide a display having a low power consumption and a long life.

What is claimed is:

1. A silole derivative represented by the following Formula (1):

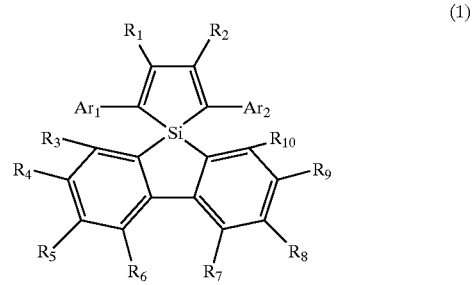

(1)

wherein $R_1$ and $R_2$ each independently represent a substituted or unsubstituted alkyl, silyl, aryl, heterocyclic or alkenyl group and may be bonded with each other at the respective terminals; $Ar_1$ and $Ar_2$ each independently represent a substituted or unsubstituted aryl or heterocyclic group; and $R_3$ to $R_{10}$ each independently represent a substituted or unsubstituted alkyl, aryl or heterocyclic group and may be bonded with each other at the respective terminals.

2. A silole derivative represented by the following Formula (2):

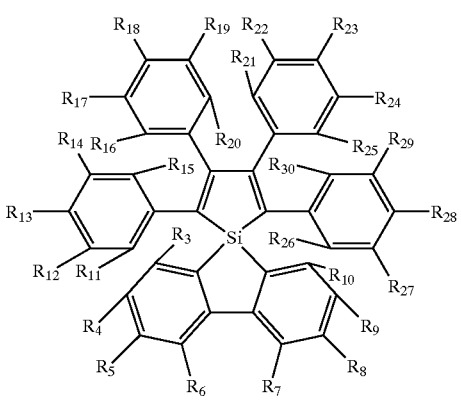

(2)

wherein $R_{11}$ to $R_{30}$ each independently represent a substituted or unsubstituted alkyl, aryl or heterocyclic group and may be bonded with each other at the respective terminals; and $R_3$ to $R_{10}$ each independently represent a substituted or unsubstituted alkyl, aryl or heterocyclic group and may be bonded with each other at the respective terminals.

3. A silole derivative represented by the following Formula (4):

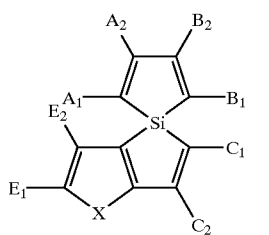

(4)

wherein $A_1$ and $A_2$ are bonded with each other to form a 5- or 6-membered ring; $B_1$ and $B_2$ are bonded with each other to form a 5- or 6-membered ring; $C_1$ and $C_2$ are bonded with each other to form a 5- or 6-membered ring; $E_1$ and $E_2$ are bonded with each other to form a 5- or 6-membered ring; X represents oxygen, sulfur or NR; and R represents hydrogen, an alkyl group or an aryl group.

4. An organic electroluminescent element containing the silole derivative as claimed in at least one of claim 1 for an electroluminescent layer.

5. An organic electroluminescent element containing the silole derivative as claimed in claim 2 for an electroluminescent layer.

6. An organic electroluminescent element containing the silole derivative as claimed in claim 3 for an electroluminescent layer.

7. A silole derivative as claimed in claim 3 in which the compound represented by the formula (4) is a compound selected from the group consisting of compounds represented by the following formulas (12), (13), (14) and (15)

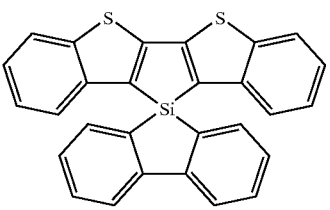

(12)

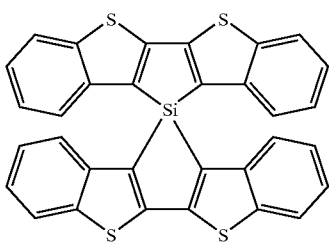

(13)

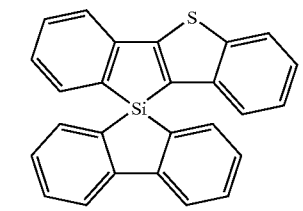

(14)

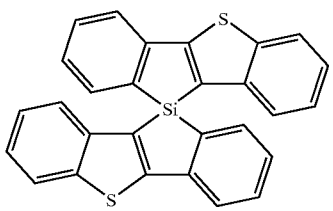

(15)

8. An organic electroluminescent element containing the silole derivative as claimed in claim 7 for an electroluminescent layer.

* * * * *